United States Patent
Ke et al.

(10) Patent No.: US 7,030,157 B2
(45) Date of Patent: Apr. 18, 2006

(54) PHARMACEUTICAL COMPOSITIONS, KITS AND METHODS COMPRISING COMBINATIONS OF ESTROGEN AGONISTS/ANTAGONISTS, ESTROGENS AND PROGESTINS

(75) Inventors: HuaZhu Ke, Ledyard, CT (US); David D. Thompson, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/206,587

(22) Filed: Jul. 26, 2002

(65) Prior Publication Data

US 2003/0065017 A1    Apr. 3, 2003

Related U.S. Application Data

(60) Provisional application No. 60/309,065, filed on Jul. 31, 2001.

(51) Int. Cl.
*A61K 31/27* (2006.01)
*A61K 31/275* (2006.01)

(52) U.S. Cl. .................................. 514/482
(58) Field of Classification Search ............ 514/482
See application file for complete search history.

(56) References Cited

U.S. PATENT DOCUMENTS

| | | | |
|---|---|---|---|
| 5,183,814 A | 2/1993 | Dukes | 31/56 |
| 5,510,357 A | 4/1996 | Palkowitz | 514/324 |
| 5,510,358 A | 4/1996 | Palkowitz | 514/324 |
| 5,534,527 A | 7/1996 | Black et al. | 31/44 |
| 5,552,401 A | 9/1996 | Cullinan et al. | 333/64 |
| 5,843,984 A | 12/1998 | Clay et al. | 43/12 |
| 5,891,868 A | 4/1999 | Cummings et al. | 31/56 |
| 5,962,475 A | 10/1999 | Schmid et al. | 31/445 |
| 6,107,331 A * | 8/2000 | MacLean et al. | 514/428 |
| 2002/0013327 A1 | 1/2002 | Lee et al. | 514/256 |
| 2002/0128276 A1 | 9/2002 | Day et al. | 514/256 |

FOREIGN PATENT DOCUMENTS

| | | |
|---|---|---|
| EP | 0665015 | 8/1995 |
| EP | 0 792 641 * | 3/1997 |
| EP | 0838464 | 4/1998 |
| EP | 0888775 | 1/1999 |
| EP | 0953568 | 11/1999 |
| EP | 0966968 | 12/1999 |
| EP | 0835868 | 8/2001 |
| EP | 1149579 | 10/2001 |
| EP | 1106179 | 6/2003 |
| WO | WO 9709348 | 3/1997 |
| WO | WO 9716434 | 5/1997 |
| WO | WO 97/31640 * | 9/1997 |
| WO | WO 9840076 | 9/1998 |
| WO | WO 9924027 | 5/1999 |
| WO | WO 9939581 | 8/1999 |
| WO | WO 9953910 | 10/1999 |
| WO | WO 9959581 | 11/1999 |
| WO | WO 9959969 | 11/1999 |
| WO | WO 9963974 | 12/1999 |
| WO | WO 0007598 | 2/2000 |
| WO | WO 0067708 | 11/2000 |
| WO | WO 0074684 | 12/2000 |
| WO | WO 0126640 | 4/2001 |
| WO | WO 0154699 | 8/2001 |

OTHER PUBLICATIONS

Berman, J.R., et al., *Urology*, "Female Sexual Dysfunction: Incidence, Pathophysiology, Evaluation, and Treatment Options", vol. 54, pp. 385-391 (1999).

International PCT Search Report relating to PCT/IB02/02763.

Ke, H., et al., *Journal of Bone and Mineral Research* "Co-Treatment of Lasofoxifene (CP-336,156) and Estrogen Inhibits Estrogen's Effect in the Uterus But Maintains the Bone Protective Effects in Ovariectomized Rats", p. S310 (2000).

(Continued)

*Primary Examiner*—San-Ming Hui
(74) *Attorney, Agent, or Firm*—Gregg C. Benson; John A. Wichtowski

(57) ABSTRACT

The present invention relates to pharmaceutical compositions, kits and methods comprising combinations of (−)-cis-6-phenyl-5-[4-(2-pyrrolidin-1-yl-ethoxy)-phenyl]-5,6,7,8-tetrahydro-naphthalene-2-ol or nontoxic pharmacologically acceptable acid addition salts thereof and estrogens. The present invention also relates to pharmaceutical compositions, kits and methods comprising combinations of (−)-cis-6-phenyl-5-[4-(2-pyrrolidin-1-yl-ethoxy)-phenyl]-5,6,7,8-tetrahydro-naphthalene-2-ol or nontoxic pharmacologically acceptable acid addition salts thereof, estrogens and progestins.

12 Claims, No Drawings

OTHER PUBLICATIONS

Rosati, R.L., et al., *J. Med. Chem.*, "Discovery and Preclinical Pharmacology of a Novel, Potent, Nonsteroidal Estrogen Receptor Agonist/Antagonist, CP-336156, a Diaryltetrahydronaphtalene", vol. 41, pp. 2928-2931 (1998).

Gegnas, L.D., *Expert Opinion on Therapeutic Patents*, "Osteoporosis Therapies", vol. 10, No. 6, pp. 833-846 (2000).

*Journal of Bone and Mineral Research*, vol. 15, No. Suppl. 1, pp. S310, 22$^{nd}$ Annual Meeting of the American Society for Bone & Mineral Research, Toronto, Ontario, Canada, Sep. 22-26, 2000.

Cooper, et al., *British Journal of Obstetrics and Gynecology*, "A Randomized Pilot Study of HRT in Patients with Breast Cancer: The Combined Effects of Tomoxifen and HRT on the Endometrium", vol. 105, Suppl. 17 p. 15 (1998).

Snyder, et al., *Am. J. Health-Syst. Pharm.* "Raloxifene Hydrochloride", vol. 57, pp. 1669-1675 (2000).

* cited by examiner

PHARMACEUTICAL COMPOSITIONS, KITS AND METHODS COMPRISING COMBINATIONS OF ESTROGEN AGONISTS/ANTAGONISTS, ESTROGENS AND PROGESTINS

CROSS REFERENCE TO RELATED APPLICATION

This application claims priority of U.S. provisional application No. 60/309,065 filed on Jul. 31, 2001.

FIELD OF THE INVENTION

The present invention relates to pharmaceutical compositions, kits and methods comprising combinations of estrogen agonists/antagonists and estrogens. The present invention also relates to pharmaceutical compositions, kits and methods comprising combinations of estrogen agonists/antagonists, estrogens and progestins.

BACKGROUND OF THE INVENTION

Various conditions and diseases have been linked to changes in hormone levels. Examples of such conditions and diseases include osteoporosis, cardiovascular disease and certain cancers. Other conditions include decreased libido, dyspareunia, sexual arousal disorder, hypoactive sexual desire disorder and vaginismus. One presently available method used to treat such diseases or conditions includes the administration of an estrogen agonist/antagonist to a patient. In addition, patients have been treated with estrogens. Such treatment is usually called hormone replacement therapy (HRT). Hormone replacement therapy has been controversial because it has been associated with increased risks for certain types of cancers.

The present invention relates to combinations of an estrogen agonist/antagonist and an estrogen, and optionally a progestin. The combinations of the present invention allow for the treatment of the diseases and conditions associated with changes in hormone levels while reducing or minimizing undesirable side effects.

SUMMARY OF THE INVENTION

The present invention provides pharmaceutical compositions comprising the compound (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

In a preferred embodiment of the pharmaceutical compositions, the (−)-cis-6-phenyl-5-[4-(2-pyrrolidin-1-yl-ethoxy)-phenyl]-5,6,7,8-tetrahydro-naphthalene-2-ol is in the form of the tartrate salt.

Also provided are pharmaceutical compositions comprising the compound (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin.

In a preferred embodiment of the compositions, the (−)-cis-6-phenyl-5-[4-(2-pyrrolidin-1-yl-ethoxy)-phenyl]-5,6,7,8-tetrahydro-naphthalene-2-ol is in the form of the tartrate salt.

Also provided are methods of treating osteoporosis in a patient, the methods comprising administering to a patient in need of such treatment a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

Also provided are methods of treating osteoporosis in a patient, the methods comprising administering to a patient in need of such treatment a therapeutically effective amonut of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin.

Also provided are methods of enhancing libido in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

Also provided are methods of enhancing libido in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene- 2-ol or a pharmacologically acceptable acid addition salt thereof, an estrogen and a progestin.

Also provided are methods of treating hypoactive sexual desire disorder in a patient, the methods comprising administering to a patient in need thereof a therapeutically effective amonut of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

Also provided are methods of treating hypoactive sexual desire disorder in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin.

Also provided are methods of treating sexual arousal disorder in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

Also provided are methods of treating sexual arousal disorder in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin.

Also provided are methods of treating dyspareunia in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

Also provided are methods of treating dyspareunia in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin.

Also provided are methods of increasing the frequency and intensity of orgasms in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

Also provided are methods of increasing the frequency and intensity of orgasms in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin.

Also provided are methods of treating vaginismus in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen.

Also provided are methods of treating vaginismus in a patient, the methods comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin.

Also provided are kits that comprises:
a) an estrogen agonist/antagonist;
b) an estrogen; and
c) instructions for administering the estrogen agonist/antagonist and estrogen to a patient to treat osteoporosis, enhance libido, treat dyspareunia, treat sexual arousal disorder, treat hypoactive sexual desire disorder, treat vaginismus, or increase the frequency or intensity of orgasms.

Also provided are methods kits that comprises:
a) an estrogen agonist/antagonist;
b) an estrogen;
c) a progestin; and
d) instructions for administering the estrogen agonist/antagonist and estrogen to a patient to treat osteoporosis, enhance libido, treat dyspareunia, treat sexual arousal disorder, treat hypoactive sexual desire disorder, treat vaginismus, or increase the frequency or intensity of orgasms.

DETAILED DESCRIPTION OF THE INVENTION

The present invention relates to pharmaceutical compositions and kits that comprise an estrogen agonist/antagonist and an estrogen. The present invention also relates to methods of treating certain conditions or diseases using a combination of an estrogen agonist/antagonist and an estrogen. In the methods of the present invention, a patient in need of treatment is administered a therapeutically effective amount of an estrogen agonist/antagonist and an estrogen.

The present invention also relates to pharmaceutical compositions and kits that comprise an estrogen agonist/antagonist, an estrogen and a progestin. The present invention also relates to methods of treating certain conditions or diseases using a combination of an estrogen agonist/antagonist, an estrogen and a progestin. In the methods of the present invention, a patient in need of treatment is administered a therapeutically effective amount of an estrogen agonist/antagonist, an estrogen and a progestin.

Examples of conditions or diseases that can be treated by administering to a patient in need thereof the combinations of the present invention include: osteopenia, osteoporosis or related bone fractures; obesity; breast cancer; endometriosis; cardiovascular disease such as atherosclerosis; benign prostatic hyperplasia; prostatic carcinoma; hypercholesterolemia; dysmenorrhea; acne; hirsutism; Alzheimer's disease; premenstrual syndrome; perimenopausal syndrome; uterine fibrosis; autoimmune diseases such as Hashimoto's thyroiditis, systemic lupus erythematosis, and Myasthenia gravis; reperfusion damage of ischemic myocardium; breast disorders such as galactorrheas, gynecomastia, hypertrophy, polythelia, mastodynia, mastaltia, and hyperprolactinermia; uterine cancer; adjuvant breast cancer; migraine; vaginal atrophy; vaginal itching; vaginal dryness; loss of sexual enjoyment; bladder infection; senile gynecomastia; diabetes; hypoglycemia; wound healing; melanoma; impotence (erectile dysfunction); inflammatory bowel disease; decreased libido; pulmonary hypertension; Turner's syndrome; alopecia; seborrhea; obsessive-compulsive disorder; smoking cessation; cessation of alcohol consumption; bulimia; anorexia nervosa; skin atrophy; skin wrinkles; skin spots; cataracts; rheumatoid arthritis; colon cancer; female sexual dysfunction including decreased libido, hypoactive sexual desire disorder, sexual arousal disorder, dyspareunia, sexual ahedonia, and vaginismus; lowering vaginal tract pH; urinary infections; undesired vaginal spasms; vaginal yeast or bacterial infections; vulvar atrophy; prolapse; urinary or anal incontinence; urinary frequency or urgency; increased intensity or frequency of orgasms; myocardial infarction; stroke; improving vascular reactivity; acute or chronic renal failure; peripheral arterial occlusive disease; coronary artery disease; Raynaud's phenomenon; musculoskelatal frailty; osteotomy; childhood idiopathic bone loss; bone loss associated with periodontis; bone healing after facial reconstruction; maxillary reconstruction; bone graft; prosthetic ingrowth enhancement; bone fracture; inhibiting bone resorption and bone turnover; preventing bone loss; preserving bone strength; osteopenia; anemia; muscle growth; andopause; hypogonadism; ovary cancer; hepatocel cancer; desmoid cancer; glioma; pancreatic cancer; renal cell cancer; and osteoarthritis.

Preferred diseases or conditions to be treated with the present combinations include osteoporosis and female sexual dysfunction. Female sexual dysfunction includes: decreased libido, hypoactive sexual desire disorder, sexual arousal disorder, dyspareunia, sexual ahedonia and vaginismus. The present combination is also preferred in the treatment or prevention of vaginal atrophy or skin atrophy including skin wrinkles and spots, and in increasing the frequency or intensity of orgasms.

Hypoactive sexual desire disorder is a disorder in which sexual fantasies and desire for sexual activity are persistently or recurrently diminished or absent, causing marked distress or interpersonal difficulties. Hypoactive sexual desire disorder may be lifelong or acquired, generalized (global) or situational (partner-specific). Sexual desire is a complex psychosomatic process based on brain activity (the "generator" or "motor" running in a rheostatic cyclic fashion), a poorly defined hormonal milieu, and cognitive scripting that includes sexual aspiration and motivation. Desynchronization of these components results in hypoactive sexual desire disorder.

The acquired form of hypoactive sexual desire disorder is commonly caused by boredom or unhappiness in a long-standing relationship, depression (which leads more often to decreased interest in sex than it does to impotence in the male or to inhibited excitement in the female), dependence on alcohol or psychoactive drugs, side effects from prescription drugs (e.g., antihypertensives, antidepressants), and hormonal deficiencies. This disorder can be secondary to impaired sexual functioning in the arousal or orgasm phase of the sexual response cycle.

Symptoms and signs of hypoactive sexual desire disorder include the patient complaining of a lack of interest in sex, even in ordinarily erotic situations. The disorder is usually associated with infrequent sexual activity, often causing serious marital conflict. Some patients have sexual encounters fairly often to please their partners and may have no difficulty with performance but continue to have sexual apathy. When boredom is the cause, frequency of sex with the usual partner decreases, but sexual desire may be normal or even intense with others (the situational form).

Sexual anhedonia (decreased or absent pleasure in sexual activity) is not an official diagnosis. It is almost always classified under hypoactive sexual desire disorder, because loss of pleasure almost always results in loss of desire (although loss of desire may occur first). The cause is likely to be depression or drugs if anhedonia is acquired and global (with all partners in all situations); interpersonal factors if anhedonia is confined to one partner or one situation; or repressive factors (e.g., guilt, shame) due to family dysfunction or childhood trauma if anhedonia is lifelong. Sexual aversion is the probable diagnosis in lifelong cases.

Sexual arousal disorder is the persistent or recurrent inability to attain or to maintain the lubrication-swelling response of sexual excitement until completion of sexual activity. This disturbance occurs despite adequate focus, intensity, and duration of sexual stimulation. The disorder may be lifelong or, more commonly, acquired and restricted to the partner. The patient's complaints are usually related to lack of orgasm, although some women report lack of excitement.

Sexual pain disorders (includes dyspareunia and vaginismus) is characterized by pain resulting from penetration and may be caused by medications which reduce lubrication, endometriosis, pelvic inflammatory disease, inflammatory bowel disease or urinary tract problems.

Dyspareunia is painful coitus or attempted coitus. Dyspareunia is usually introital but may also occur before, during, or after intercourse. Causes include menopausal involution with dryness and thinning of the mucosa. Pain during or after coitus is the chief complaint.

The term "patient" means a mammal having one or more of the conditions or diseases or at risk of having one or more of the conditions or diseases disclosed herein. Preferred patients are humans. An especially preferred patient is a postmenopausal woman.

The term "treat" means to ameliorate or prevent the onset of or more symptom of a disease or condition.

The above-identified diseases and conditions can be treated using a combination of an estrogen agonist/antagonist and an estrogen, or the combination of an estrogen agonist/antagonist, an estrogen and a progestin.

A combination of an estrogen agonist/antagonist may comprise one or more estrogen agonist/antagonist and one or more estrogen. For example, a combination may contain one estrogen agonist/antagonist and two estrogens. Alternatively, the combination may contain more than one estrogen agonist/antagonist and one estrogen.

The combinations of the present invention can be administered to a patient all at once, such as in the same tablet, or in multiple tablets taken at the same time. Alternatively the estrogen agonist/antagonist can be taken at one time and the estrogen taken at another time. For convenience, it is preferable to take both the estrogen agonist/antagonist and the estrogen at the same time. There are many ways in which the combinations of the present invention can be administered to a patient. It is contemplated that the present invention encompass the various ways of administering the estrogen agonists/antagonists and estrogens.

Also provided by the present invention are combinations for the treatment or prevention of the above-mentioned conditions or diseases that comprise an estrogen agonist/antagonist, an estrogen and a progestin. The combination can be administered in the same dosage form at the same time, in different dosage forms at the same time, or in different dosage forms at different times. All variations of administration methods and administration times are contemplated. For example, the estrogen agonist/antagonist, estrogen and progestin can be administered in separate tablets or capsules. In another embodiment, the estrogen agonist/antagonist and estrogen can be administered in one tablet and the progestin in a second tablet. It is also possible to use different dosage forms to administer the components of the combination. For example, some components can be administered by tablet or capsule and others delivered transdermally, such as by a patch. Nasal administration is also contemplated for the combinations of the present invention. It is also noted that more than one estrogen agonist/antagonist, estrogen or progestin can be used in the combinations.

The term "postmenopausal women" is defined to include not only women of advanced age who have passed through menopause, but also women who have been hysterectomized or for some other reason have suppressed estrogen production, such as those who have undergone long-term administration of corticosteroids, suffer from Cushions' syndrome or have gonadal dysgenesis.

An "estrogen agonist/antagonist" is a compound that affects some of the same receptors that estrogen does, but not all, and in some instances, it antagonizes or blocks estrogen. It is also known as a "selective estrogen receptor modulator" (SERM). Estrogen agonists/antagonists may also be referred to as antiestrogens although they have some estrogenic activity at some estrogen receptors. Estrogen agonists/antagonists are therefore not what are commonly referred to as "pure antiestrogens". Antiestrogens that can also act as agonists are referred to as Type I antiestrogens. Type I antiestrogens activate the estrogen receptor to bind tightly in the nucleus for a prolonged time but with impaired receptor replenishment (Clark, et al., *Steroids* 1973;22:707, Capony et al., *Mol Cell Endocrinol*, 1975;3:233).

Preferred estrogen agonists/antagonists of the present invention include the compounds described in U.S. Pat. No. 5,552,412. Those compounds are described by formula (I) given below:

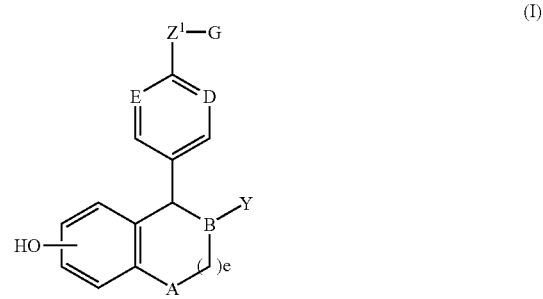

wherein:
  A is selected from $CH_2$ and NR;
  B, D and E are independently selected from CH and N;
  Y is
   (a) phenyl, optionally substituted with 1–3 substituents independently selected from $R^4$;
   (b) naphthyl, optionally substituted with 1–3 substituents independently selected from $R^4$;
   (c) $C_3$–$C_8$ cycloalkyl, optionally substituted with 1–2 substituents independently selected from $R^4$;
   (d) $C_3$–$C_8$ cycloalkenyl, optionally substituted with 1–2 substituents independently selected from $R^4$;
   (e) a five membered heterocycle containing up to two heteroatoms selected from the group consisting of —O—, —$NR^2$— and —$S(O)_n$—, optionally substituted with 1–3 substituents independently selected from $R^4$;
   (f) a six membered heterocycle containing up to two heteroatoms selected from the group consisting of —O—, —$NR^2$— and —$S(O)_n$— optionally substituted with 1–3 substituents independently selected from $R^4$; or
   (g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;
  $Z^1$ is
   (a) —$(CH_2)_p$ $W(CH_2)_q$—;
   (b) —$O(CH_2)_p$ $CR^5R^6$—;
   (c) —$O(CH_2)_p W(CH_2)_{q-}$;
   (d) —$OCHR^2CHR^3$—; or
   (e) —$SCHR^2CHR^3$—;
  G is
   (a) —$NR^7R^8$;

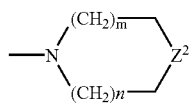
   (b)

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
   (c) a bicyclic amine containing five to twelve carbon atoms, either bridged or fused and optionally substituted with 1–3 substituents independently selected from $R^4$; or
  $Z^1$ and G in combination may be

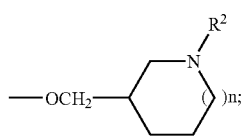

W is
   (a) —$CH_2$—;
   (b) —CH=CH—;
   (c) —O—;
   (d) —$NR^2$—;
   (e) —$S(O)_n$—;

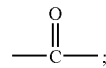
   (f)

(g) —$CR^2(OH)$—;
   (h) —$CONR^2$—;
   (i) —$NR^2CO$—;

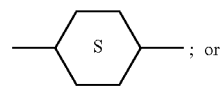
   (j) ; or (k) —C≡C—;
  R is hydrogen or $C_1$–$C_6$ alkyl;
  $R^2$ and $R^3$ are independently
   (a) hydrogen; or
   (b) $C_1$–$C_4$ alkyl;
  $R^4$ is
   (a) hydrogen;
   (b) halogen;
   (c) $C_1$–$C_6$ alkyl;
   (d) $C_1$–$C_4$ alkoxy;
   (e) $C_1$–$C_4$ acyloxy;
   (f) $C_1$–$C_4$ alkylthio;
   (g) $C_1$–$C_4$ alkylsulfinyl;
   (h) $C_1$–$C_4$ alkylsulfonyl;
   (i) hydroxy ($C_1$–$C_4$)alkyl;
   (j) aryl ($C_1$–$C_4$)alkyl;
   (k) —$CO_2H$;
   (l) —CN;
   (m) —CONHOR;
   (n) —$SO_2NHR$;
   (o) —$NH_2$;
   (p) $C_1$–$C_4$ alkylamino;
   (q) $C_1$–$C_4$ dialkylamino;
   (r) —$NHSO_2R$;
   (s) —$NO_2$;
   (t) —aryl; or
   (u) —OH;
  $R^5$ and $R^6$ are independently $C_1$–$C_8$ alkyl or together form a $C_3$–$C_{10}$ carbocyclic ring;
  $R^7$ and $R^8$ are independently
   (a) phenyl;
   (b) a $C_3$–$C_{10}$ carbocyclic ring, saturated or unsaturated;
   (c) a $C_3$–$C_{10}$ heterocyclic ring containing up to two heteroatoms, selected from —O—, —N— and —S—;
   (d) H;
   (e) $C_1$–$C_6$ alkyl; or
   (f) form a 3 to 8 membered nitrogen containing ring with $R^5$ or $R^6$;
  $R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, esters, quaternary ammonium salts and prodrugs thereof.

By halo is meant chloro, bromo, iodo, or fluoro or by halogen is meant chlorine, bromine, iodine or fluorine.

By alkyl is meant straight chain or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

Additional preferred compounds of the invention also disclosed in U.S. Pat. No. 5,552,412 are of the formula (IA):

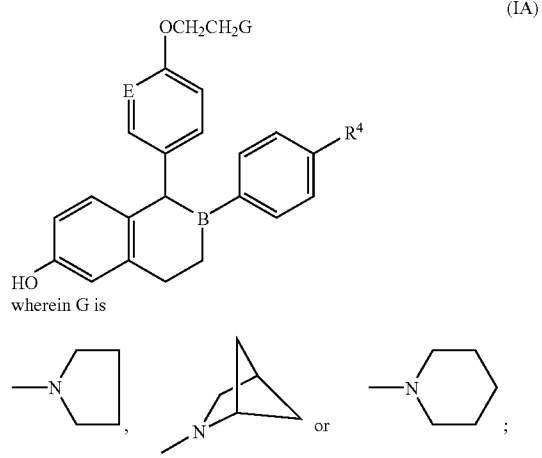

wherein G is $R^4$ is H, OH, F, or Cl; and B and E are independently selected from CH and N.

Especially preferred compounds for the compositions, methods and kits of the invention are:
cis-6-(4-fluoro-phenyl)-5-[4-(2-piperidin-1-yl-ethoxy)-phenyl]-5,6,7,8-tetrahydro-naphthalene-2-ol;
(−)-cis-6-phenyl-5-[4-(2-pyrrolidin-1-yl-ethoxy)-phenyl]-5,6,7,8-tetrahydro-naphthalene-2-ol;
cis-6-phenyl-5-[4-(2-pyrrolidin-1-yl-ethoxy)-phenyl]-5,6,7,8-tetrahydro-naphthalene-2-ol;
cis-1-[6'-pyrrolidinoethoxy-3'-pyridyl]-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-[4-(2-piperidin-1-yl-ethoxy)-phenyl]-5,6,7,8-tetrahydro-naphthalene-2-ol; and
1-(4'-pyrrolidinoethoxyphenyl)-2-phenyl-6-hydroxy-1,2,3,4-tetrahydroisoquinoline and pharmaceutically acceptable salts thereof. An especially preferred salt of (−)-cis-6-phenyl-5-[4-(2-pyrrolidin-1-yl-ethoxy)-phenyl]-5,6,7,8-tetrahydro-naphthalene-2-ol is the tartrate salt.

Other preferred estrogen agonists/antagonists are disclosed in U.S. Pat. No. 5,047,431. The structure of these compounds is given by formula (II) below:

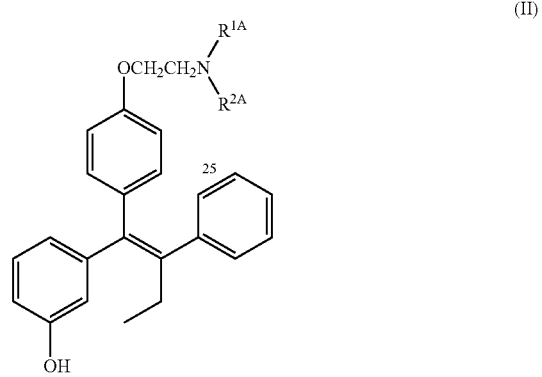

wherein
$R^{1A}$ and $R^{2A}$ may be the same or different and are either H, methyl, ethyl or a benzyl group; and optical or geometric isomers thereof; and pharmaceutically acceptable salts, N-oxides, esters, quaternary ammonium salts, and prodrugs thereof.

Additional preferred estrogen agonists/antagonists are tamoxifen:
(ethanamine,2-[-4-(1,2-diphenyl-1-butenyl)phenoxy]-N,N-dimethyl, (Z)-2-, 2-hydroxy-1,2,3-propanetricarboxylate (1:1)) and other compounds as disclosed in U.S. Pat. No. 4,536,516; 4-hydroxy tamoxifen (i.e., tamoxifen wherein the 2-phenyl moiety has a hydroxy group at the 4 position) and other compounds as disclosed in U.S. Pat. No. 4,623,660; raloxifene: (methanone, [6-hydroxy-2-(4-hydroxyphenyl)benzo[b]thien-3-yl][4-[2-(1-piperidinyl) ethoxy]phenyl]-,hydrochloride) and other compounds as disclosed in U.S. Pat. Nos. 4,418,068; 5,393,763; 5,457,117; 5,478,847 and 5,641,790; toremifene: (ethanamine, 2-[4-(4-chloro-1,2-diphenyl-1-butenyl)phenoxy]-N,N-dimethyl-, (Z)-, 2-hydroxy-1,2,3-propanetricarboxylate (1:1) and other compounds as disclosed in U.S. Pat. Nos. 4,696,949 and 4,996,225; centchroman: 1-[2-[[4-(-methoxy-2,2, dimethyl-3-phenyl-chroman-4-yl)-phenoxy]-ethyl]-pyrrolidine and other compounds as disclosed in U.S. Pat. No. 3,822,287; idoxifene: pyrrolidine, 1-[-[4-[[1-(4-iodophenyl)-2-phenyl-1-butenyl]phenoxy]ethyl] and other compounds as disclosed in U.S. Pat. No. 4,839,155; 6-(4-hydroxy-phenyl)-5-[4-(2-piperidin-1-yl-ethoxy)-benzyl]-naphthalen-2-ol and other compounds as disclosed in U.S. Pat. No. 5,484,795; and {4-[2-(2-azabicyclo[2.2.1]hept-2-yl)-ethoxy]-phenyl}-[6-hydroxy-2-(4-hydroxy-phenyl)-benzo[b]thiophen-3-yl]-methanone and other compounds as disclosed in published international patent application WO 95/10513. Other preferred compounds include GW 5638 and GW 7604, the synthesis of which is described in Willson et al., *J. Med. Chem.*, 1994;37:1550–1552.

Further preferred estrogen agonists/antagonists include EM-652 (as shown in formula (III) and EM-800 (as shown in formula (IV)). The synthesis of EM-652 and EM-800 and the activity of various enantiomers is described in Gauthier et al., *J. Med. Chem.*, 1997;40:2117–2122.

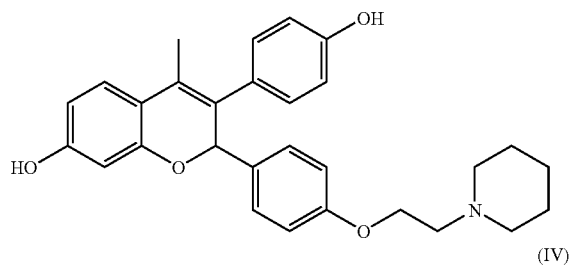

(III)

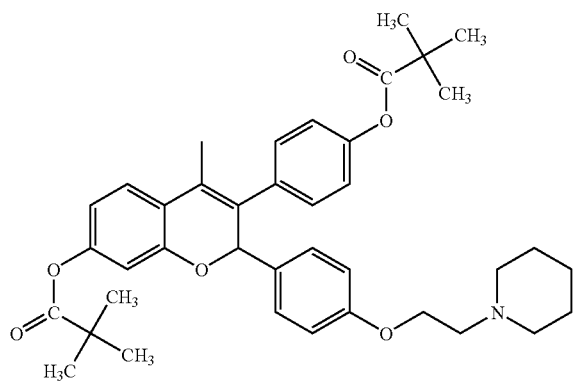

(IV)

Further preferred estrogen agonists/antagonists include TSE-424 and other compounds disclosed in U.S. Pat. Nos. 5,998,402, 5,985,910, 5,780,497, 5,880,137, and European Patent Application EP 0802183 A1 including the compounds of the formulas V and VI, below:

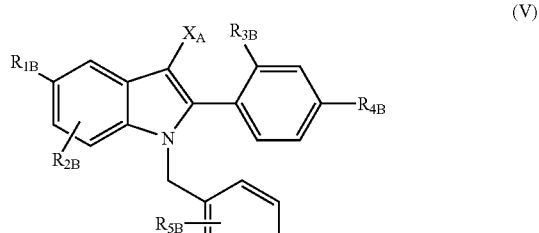

(V)

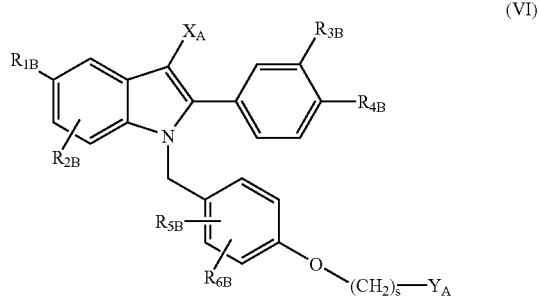

(VI)

wherein:

$R_{1B}$ is selected from H, OH or the $C_1$–$C_{12}$ esters (straight chain or branched) or $C_1$–$C_{12}$ (straight chain or branched or cyclic) alkyl ethers thereof, or halogens; or $C_1$–$C_4$ halogenated ethers including triflouromethyl ether and trichloromethyl ether.

$R_{2B}$, $R_{3B}$, $R_{4B}$, $R_{5B}$, and $R_{6B}$ are independently selected from H, OH or the $C_1$–$C_{12}$ esters (straight chain or branched) or $C_1$–$C_{12}$ alkyl ethers (straight chain or branched or cyclic) thereof, halogens, or $C_1$–$C_4$ halogenated ethers including triflouromethyl ether and trichloromethyl ether, cyano, $C_1$–$C_6$ alkyl (straight chain or branched), or trifluoromethyl, with the proviso that, when $R_{1B}$ is H, $R_{2B}$ is not OH.

$X_A$ is selected from H, $C_1$–$C_6$ alkyl, cyano, nitro, triflouromethyl, and halogen;

s is 2 or 3;

$Y_A$ is selected from:

a) the moiety:

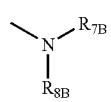

wherein $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$;

b) a five-membered saturated, unsaturated or partially unsaturated heterocycle containing up to two heteroatoms selected from the group consisting of —O—, —NH—, —N($C_1$–$C_4$ alkyl)-, —N═, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, —$CO_2H$—, —CN—, —$CONHR_{1B}$—, —$NH_2$—, $C_1$–$C_4$ alkylamino, di($C_1$–$C_4$)alkylamino, —$NHSO_2R_{1B}$—, —$NHCOR_{1B}$—, —$NO_2$, and phenyl optionally substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1$–$C_4$ alkyl)-, —N═, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, —$CO_2H$—, —CN—, —$CONHR_1$—, —$NH_2$—, $C_1$–$C_4$ alkylamino, di($C_1$–$C_4$)alkylamino, —$NHSO_2R_{1B}$—, —$NHCOR_{1B}$—, —$NO_2$, and phenyl optionally substituted with 1–3 ($C_1$–$C_4$)alkyl;

d) a seven-membered saturated, unsaturated or partially unsaturated heterocycle containing up to two heteroatoms selected from the group consisting of —O—, —NH—, —N($C_1$–$C_4$ alkyl)-, —N═, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, —$CO_2H$—, —CN—, —$CONHR_{1B}$—, —$NH_2$—, $C_1$–$C_4$ alkylamino, di($C_1$–$C_4$)alkylamino, —$NHSO_2R_{1B}$—, —$NHCOR_{1B}$—, —$NO_2$, and phenyl optionally substituted with 1–3 ($C_1$–$C_4$)alkyl; or e) a bicyclic heterocycle containing from 6–12 carbon atoms either bridged or fused and containing up to two heteroatoms selected from the group consisting of —O—, —NH—, —N($C_1$–$C_4$ alkyl)-, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —$CONHR_{1B}$—, —$NH_2$, —N=, $C_1$–$C_4$ alkylamino, di($C_1$–$C_4$)alkylamino, —$NHSO_2R_{1B}$—, —$NHCOR_{1B}$—, —$NO_2$, and phenyl optionally substituted with 1–3 ($C_1$–$C_4$) alkyl; and optical or geometric isomers thereof; and nontoxic pharmacologically acceptable acid addition salts, N-oxides, esters, quaternary ammonium salts, and prodrugs thereof.

The more preferred compounds of this invention are those having the general structures V or VI, above, wherein:

$R_{1B}$ is selected from H, OH or the $C_1$–$C_{12}$ esters or alkyl ethers thereof, and halogen;

$R_{2B}$, $R_{3B}$, $R_{4B}$, $R_{5B}$, and $R_{6B}$ are independently selected from H, OH or the $C_1$–$C_{12}$ esters or alkyl ethers thereof, halogen, cyano, $C_1$–$C_6$ alkyl, or trihalomethyl, preferably trifluoromethyl, with the proviso that, when $R_{1B}$ is H, $R_{2B}$ is not OH;

$X_A$ is selected from H, $C_1$–$C_6$ alkyl, cyano, nitro, triflouromethyl, and halogen;

$Y_A$ is the moiety:

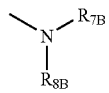

$R_{7B}$ and $R_{8B}$ are selected independently from H, $C_1$–$C_6$ alkyl, or combined by —$(CH_2)_w$—, wherein w is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$) alkyl, —$CO_2H$, —CN, —$CONH(C_1$–$C_4)$, —$NH_3$, $C_1$–$C_4$ alkylamino, $C_1$–$C_4$ dialkylamino, —$NHSO_2(C_1$–$C_4)$, —$HCO(C_1$–$C_4)$, and —$NO_3$; and optical and geometric isomers thereof; and nontoxic pharmacologically acceptable acid addition salts, N-oxides, esters, quaternary ammonium salts, and prodrugs thereof.

The rings formed by a concatenated $R_{7B}$ and $R_{8B}$, mentioned above, may include, but are not limited to, aziridine, azetidine, pyrrolidine, piperidine, hexamethyleneamine or heptamethyleneamine rings.

The most preferred compounds of structural formulas V and VI, above, are those wherein $R_{1B}$ is OH; $R_{2B}$–$R_{6B}$ are as defined above; $X_A$ is selected from the group of Cl, $NO_2$, CN, $CF_3$, or $CH_3$; $Y_A$ is the moiety

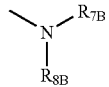

and $R_{7B}$ and $R_{8B}$ are concatenated together as —$(CH_2)_t$—, wherein t is an integer of from 4 to 6, to form a ring optionally substituted by up to three subsituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONH(C_1$–$C_4)$alkyl, —$NH_2$, $C_1$–$C_4$ alkylamino, di($C_1$–$C_4$)alkylamino, —$NHSO_2(C_1$–$C_4)$alkyl, —$NHCO(C_1$–$C_4)$alkyl, and —$NO_2$; and optical and geometric isomers thereof; and nontoxic pharmacologically acceptable acid addition salts, N-oxides, esters, quaternary ammonium salts, and prodrugs thereof including the compound, TSE-424, of formula (Va) below:

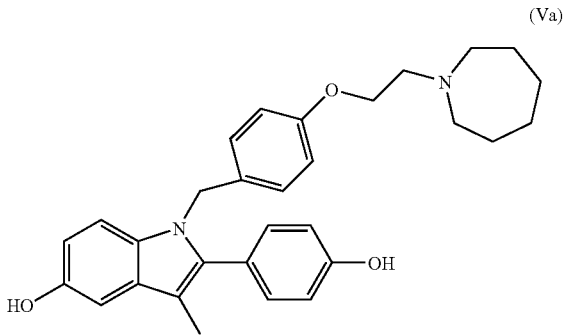

(Va)

Estrogens useful in the combinations of this invention include estrone, estriol, equilin, estradiene, equilenin, ethinyl estradiol, 17β-estradiol, 17α-dihydroequilenin, 17β-dihydroequilenin (U.S. Pat. No. 2,834,712), 17α-dihydroequilin, 17β-dihydroequilin, menstranol and conjugated estrogenic hormones, such as those in Wyeth-Ayerst Laboratories' Premarin® products. Phytoestrogens, such as equol or enterolactone, may also be used in the present formulations and methods. Esterified estrogens, such as those sold by Solvay Pharmaceuticals, Inc. under the Estratab® tradename, may also be used in the present combinations. Also preferred for use in the present invention are the salts of the applicable estrogens, most preferably the sodium salts. Examples of these preferred salts are sodium estrone sulfate, sodium equilin sulfate, sodium 17alpha-dihydroequilin sulfate, sodium 17alpha-estradiol sulfate, sodium delta8,9-dehydroestrone sulfate, sodium equilenin sulfate, sodium 17beta-estradiol sulfate, sodium 17beta-dihydroequilin sulfate, estrone 3-dosium sulfate, equilin 3-sodium sulfate, 17alpha-dihydroequilin 3-sodium sulfate, 3beta-Hydroxy-estra-5(10),7-dien-17-one 3-sodium sulfate, 5alpha-pregnan-3beta-20R-diol 20-sodium sulfate, 5alpha-pregnn-3beta, 16alpha-diol-20-one 3-sodium sulfate, delta(8,9)-dehydroestrone 3-sodium sulfate, estra-3beta, 17alpha-diol 3-sodium sulfate, 3beta-Hydroxy-estr-5(10)-en-17-one 3-sodium sulfate or 5alpha-Pregnan-3beta, 16alpha,20R-triol 3-sodium sulfate. Preferred salts of estrone include, but are not limited to, the sodium and piperate salts. Other salts are described below.

Another type of compound that is useful in the present invention are the synthetic steroids such as tibolone (Livial®). The combination of an estrogen agonist/antagonist, particularly (–)-cis-6-phenyl-5-[4-(2-pyrrolidin-1-yl-ethoxy)-phenyl]-5,6,7,8-tetrahydro-naphthalene-2-ol or a nontoxic pharmacologically acceptable acid addition salt thereof, in combination with tibolone for the treatment of osteoporosis, to enhance libido, treat dyspareunia, treat sexual arousal disorder, treat hypoactive sexual desire disorder, treat vaginismus, or increase the frequency or intensity of orgasms is preferred. The use of tibolone and an estrogen agonist/antagonist can also optionally include a progestin.

Progestins are familiar to those skilled in the art. Examples of specific progestins that can be used in the present invention include, but are not limited to, levonorgestrel, norethindrone, ethynodiol, desogestrel, norgestrel, norgestimate, and medroxyprogesterone. In pharmaceutical compositions, it is common to use a salt of the progestins, which salts are described below.

The pharmaceutically acceptable acid addition salts of the estrogen agonists/antagonists, estrogens and progestins, if applicable, include salts formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid.

These salts may be formed by reacting the compound with a suitable acid. The salts are frequently formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it. A preferred salt of (−)-cis-6-phenyl-5-[4-(2-pyrrolidin-1-yl-ethoxy)-phenyl]-5,6,7,8-tetrahydro-naphthalene-2-ol is the D-(−)-tartrate salt. It will also be recognized that it is possible to administer amorphous forms of the estrogen agonists/antagonists, estrogens and progestins.

One of ordinary skill in the art will recognize that certain estrogen agonist/antagonists, estrogen or progestins will contain one or more atoms which may be in a particular stereochemical, tautomeric, or geometric configuration, giving rise to stereoisomers, tautomers and configurational isomers. All such isomers and mixtures thereof are included in this invention. Hydrates and solvates of the compounds of this invention are also contemplated.

The subject invention also includes isotopically-labeled estrogen agonists/antagonists, estrogens or progestins, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

Pharmaceutical chemists will easily recognize that physiologically active compounds which have accessible hydroxy groups are frequently administered in the form of pharmaceutically acceptable esters. The literature concerning such compounds, such as estradiol, provides a great number of instances of such esters. The compounds of this invention are no exception in this respect, and can be effectively administered as an ester, formed on the hydroxy groups. It is possible to adjust the rate or duration of action of the compound by appropriate choices of ester groups.

As used herein, the term "effective amount" means an amount of compound of the compositions, kits and methods of the present invention that is capable of treating the described conditions or diseases. The specific dose of a compound administered according to this invention will, of course, be determined by the particular circumstances surrounding the case including, for example, the compound administered, the route of administration, the state of being of the patient, and the severity of the pathological condition being treated.

The dose of a compound of this invention to be administered to a subject is rather widely variable and subject to the judgement of the attending physician. It should be noted that it may be necessary to adjust the dose of a compound when it is administered in the form of a salt, such as a laureate, the salt forming moiety of which has an appreciable molecular weight.

The following dosage amounts and other dosage amounts set forth elsewhere in this description and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject and the presence of diseases, e.g., diabetes, in the subject. All doses set forth herein, and in the appendant claims, are daily doses.

The general range of effective administration rates of the estrogen agonists/antagonists is from about 0.001 mg/day to about 200 mg/day. A preferred rate range is from about 0.010 mg/day to 100 mg/day. Of course, it is often practical to administer the daily dose of compound in portions, at various hours of the day. However, in any given case, the amount of compound administered will depend on such factors as the potency of the specific estrogen agonist/antagonist, the solubility of the compound, the formulation used and the route of administration.

An acceptable dosage range for estrogens includes, but is not limited to, about 0.001 mg/day to about 100 mg/day. A preferred estrogen dosage range includes, but is not limited to about 0.010 mg/day to about 2 mg/day. An acceptable dosage range for progestins includes, but is not limited to about 0.001 mg/day to about 1000 mg/day. A preferred dosage range for the progestins is about 0.1 mg/day to about 500 mg/day.

Methods of formulation are well known in the art and are disclosed, for example, in *Remington: The Science and Practice of Pharmacy*, Alfonso R. Gennaro, Mack Publishing Company, Easton, Pa., 19th Edition (1995). Pharmaceutical compositions for use within the present invention can be in the form of sterile, non-pyrogenic liquid solutions or suspensions, coated capsules, suppositories, lyophilized powders, transdermal patches or other forms known in the art.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which facilitate the disintegration of a tablet to release a compound when the tablet becomes wet. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavorant and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Topical formulations may be designed to yield delayed and/or prolonged percutaneous absorption of a compound. Even the parenteral preparations may be made long-acting, by dissolving or suspending the compound in oily or emulsified vehicles which allow it to disperse only slowly in the serum.

The term "prodrug" means a compound that is transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the *A.C.S. Symposium Series,* and in *Bioreversible Carriers in Drug Design,* ed. Edward B. Roche, American Pharmaceutical Association and Pergamon Press, 1987.

For example, when a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as α-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, when a compound of the present invention comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$)alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$–$C_6)alkyl)_2$ or glycosyl (the radical resulting from the removal of a hydroxyl group of the hemiacetal form of a carbohydrate).

When a compound of the present invention comprises an amine functional group, a prodrug can be formed by the replacement of a hydrogen atom in the amine group with a group such as $R^X$-carbonyl, $R^X$O-carbonyl, $NR^X R^{X_1}$-carbonyl where $R^X$ and $R^{X_1}$ are each independently (($C_1$–$C_{10}$) alkyl, ($C_3$–$C_7$)cycloalkyl, benzyl, or $R^X$-carbonyl is a natural α-aminoacyl or natural α-aminoacyl-natural α-aminoacyl, —C(OH)C(O)$OY^X$ wherein ($Y^X$ is H, ($C_1$–$C_6$)alkyl or benzyl), —C($OY^{X0}$) $Y^{X1}$ wherein $Y^{X0}$ is ($C_1$–$C_4$) alkyl and $Y^{X1}$ is (($C_1$–$C_6$)alkyl, carboxy($C_1$–$C_6$)alkyl, amino($C_1$–$C_4$)alkyl or mono-N- or di-N,N-($C_1$–$C_6$)alkylaminoalkyl, —C($Y^{X2}$) $Y^{X3}$ wherein $Y^{X2}$ is H or methyl and $Y^{X3}$ is mono-N- or di-N,N-($C_1$–$C_6$)alkylamino, morpholino, piperidin-1-yl or pyrrolidin-1-yl.

Advantageously, the present invention also provides kits for use by a consumer to treat the diseases and conditions mentioned herein, particularly osteoporosis, decreased libido, sexual arousal disorder, hypoactive sexual desire disorder, sexual anhedonia, dyspareunia, vaginismus, or increase the frequency or intensity of orgasms.

In one embodiment, the kit comprises an estrogen agonist/antagonist; an estrogen; and instructions for administering the estrogen agonist/antagonist and estrogen to a patient to treat osteoporosis, enhance libido, treat dyspareunia, treat sexual arousal disorder, treat hypoactive sexual desire disorder, treat vaginismus, or increase the frequency or intensity of orgasms. The estrogen agonist/antagonist may be contained in the same container or package or in different containers or packages than the estrogen.

In another embodiment, a kit comprises an estrogen agonist/antagonist; an estrogen; a progestin; and instructions for administering the estrogen agonist/antagonist, estrogen and progestin to a patient to treat osteoporosis, enhance libido, treat dyspareunia, treat sexual arousal disorder, treat hypoactive sexual desire disorder, treat vaginismus, or increase the frequency or intensity of orgasms. The estrogen agonist/antagonist may be contained in the same container or package as the estrogen or progestin, or the estrogen agonist/antagonist, estrogen and progestin can be in different containers or packages.

It is noted that each of the components of the combinations can be in the same container or in different containers. For example, two or more components can be in the same container with the third being in another container. All variations are envisioned. Also, when more than one compound of the same type is used (i.e., two or more estrogen agonists/antagonists), the compounds may be in the same dosage form in the same container or in different dosage forms in the same container or in different containers. Again, all variations are envisioned.

A "kit" as used in the instant application includes one or more containers for containing the pharmaceutical compositions comprising the estrogen agonist/antagonist, estrogen and progestin, and may also include divided containers such as a divided bottle or a divided foil packet. The containers can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The containers employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc . . . . "Second Week, Monday, Tuesday, . . ." etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The combinations of the present invention are preferably dosed daily, including once, twice or three times a day. However, it is contemplated that the combination or components of the combination may not be administered daily. For example, the estrogen agonist/antagonist could be administered one each week, once each month or every other day. Each component of the combination could be administered non-daily. It is also possible that some components of the combination could be administered daily while other are administered non-daily. A preferred administration route employs the use of a single daily dosage form such as tablets or capsules that are administered on a daily basis.

The example presented herein is intended to illustrate specific aspects of the invention and are not intended to limit the specification or the claims in any manner.

All references and patents cited herein are incorporated by reference.

EXAMPLE

Estrogens have been proven to have numerous beneficial effects on the skeleton and cardiovascular systems in postmenopausal women (1). However, estrogens also have undesirable side-effects including stimulation of uterine tissue (1). These undesirable side-effects lead to poor compliance among postmenopausal women (1).

Tissue selective estrogen receptor modulators (SERMs) are currently being investigated as alternatives to estrogens for the prevention and treatment of postmenopausal osteoporosis (2–5). SERMs have been proven to be beneficial to bone due to their ability to prevent bone loss as well as preserve bone strength in ovariectomized (OVX) rats and in postmenopausal women (2-5). These bone protective effects were achieved by inhibiting the resorption and turnover that occurs due to decreased estrogen levels as a result of OVX (1,2) or menopause.

Lasofoxifene, which is (−)-cis-6-phenyl-5-[4-(2-pyrrolidin-1-yl-ethoxy)-phenyl]-5,6,7,8-tetrahydro-naphthalene-2-ol, tartrate salt (LAS) is currently under clinical investigation for both the prevention and treatment of postmenopausal osteoporosis. We have previously reported that LAS bound selectively and with high affinity with both estrogen receptors $\alpha$ and $\beta$, which is similar to the binding of estradiol (EE). Furthermore, LAS antagonizes the proliferation of breast cancer in vivo and uterine cancer cell lines in vitro.

The purpose of this study was to test whether (a) LAS can antagonize estrogen's uterine stimulation effects, and (b) LAS can synergize or antagonize estrogen's bone protective effect in OVX rats.

MATERIALS AND METHODS

Animals and Study Design

Sprague-Dawley female rats at 5.5 months of age were used in this study. Rats underwent either sham-operation or bilateral ovariectomy. Beginning at 1 day post-surgery, the rats were treated (daily gavage) with vehicle, 17α-ethanyl estradiol (EE) alone, lasofoxifene (LAS) alone, or combination of both EE and LAS for 28 days, according to the following protocol.

Group I. Sham+Vehicle (0.5% Methylcellulose)
Group II. OVX+Vehicle (0.5% Methylcellulose)
Group III. OVX+EE at 0.03 mg/kg
Group IV. OVX+LAS at 0.1 mg/kg
Group V. OVX+EE at 0.03 mg/kg+LAS at 0.1 mg/kg There were 10 rats in each group. All rats received subcutaneous injections of the fluorescent marker, calcein, at 10 mg/kg on days 12 and 2 before necropsy in order to determine dynamic bone changes. After 28 days of treatment, the rats were necropsy, and the following endpoints were determined.

Body weight
Total serum cholesterol (TSC)
Uterine wet weight
Peripheral quantitative computerized tomography (pQCT). A pQCT X-ray machine (Stratec XCT Reasearch M, Norland Medical Systems, Fort Atkinson, Wis.) with version 5.40 was used to scan femurs from this study. A cross sectional slice 1 mm in thickness was taken of the femoral metaphysis approximately 5 mm proximal to the distal end. A voxel size of 0.10 mm was used, with dimensions of 100×100×1000 micometers. Cortical bone was defined and analyzed using contour mode 2 and cortical mode 4. The cortical shell was distinguished from soft tissue with an outer threshold setting of 349 mg/cm$^3$. Furthermore, cortical bone along the endocortical surface was determined with an inner threshold of 529 mg/cm$^3$. In order to determine the presence of trabecular bone, peel mode 4 was used. (Sub)Cortical bone was distinguished from cancellous bone with a threshold setting of 655 mg/cm$^3$. An additional concentric peel was also used to eliminate (sub)cortical bone from any analyses. For trabecular and cortical bone, content, density and area were determined. Repositioning resulted in precision ranging from 0.99% to 3.49%.

Proximal tibial metaphyseal cancellous bone histomorphometry. Tibiae were removed upon necropsy and removed of tissue. The proximal portion of the tibia was fixed in 70% ethanol, dehydrated in graded concentrations of ethanol, defatted in acetone, and embedded in methyl methacrylate. Four and ten μm sections were taken to determine several histomorphometric parameters with an Image Analysis System (Osteomeasure, Inc., Atlanta, Ga.). The 10 μm remained unstained while the 4 μm section was stained with modified Masson's Trichrome stain (5,6,7).

Statistics

Statistics were calculated using StatView 4.0 software (Abacus Concepts, Inc., Berkeley, Calif.). Fisher's PLSD was used to determine the differences between each group. A p value<0.05 was considered a significant difference.

RESULTS

Body Weight Gain

OVX resulted in a significantly higher gain (+146%) compared to sham controls. EE, LAS and co-administration resulted in body weight gain that was both significantly lower than sham and OVX controls. Furthermore, rats treated with LAS or both LAS and EE gained significantly less than those rats treated with EE alone.

Total Serum Cholesterol (TSC)

OVX caused a significant increase in TSC compared with sham controls. Treatment with EE completely prevented this increase. LAS not only prevented the OVX-induced increase in TSC, but also significantly decreased TSC to a level below both sham controls and rats treated with EE. Rats treated with both EE and LAS significantly decreased TSC compared with sham and OVX controls.

Uterine Wet Weight

Uterine wet weight was significantly lower in OVX controls compared with sham controls. Treatment with EE in OVX rats maintained the uterine wet weight at the level of sham controls. LAS and the co-administration groups resulted in uterine weight significantly higher than OVX controls but significantly lower than sham controls and OVX rats treated with EE. These results indicated that LAS blocked the agonistic effects of EE in the uterus of OVX rats.

pQCT of the Distal Femur

OVX resulted in a significant decrease in total density and cortical content. EE or LAS alone, or co-administration of EE and LAS completely prevented the OVX-induced decrease in these parameters.

Bone mass in the co-administration group was not different from the bone mass of OVX rats treated with either EE or LAS alone, indicating that there was no synergistic or antagonistic effect in bone mass when EE and LAS are given in combination at their fully efficacious doses.

Dynamic Histomorphometry of the Proximal Tibial Metaphysis

Compared with sham controls, OVX induced a significant increase in osteoclast number (Oc.N/BS), osteoclast surface (Oc.S/BS), mineral apposition rate (MAR), mineralizing surface (MS/BS), and bone formation rate (BFR/BS). Treatment of OVX rats with EE alone, LAS alone, or combination of both EE and LAS completely prevented these changes. There was no significant difference in above parameters among sham controls, OVX rats treated with EE alone, LAS alone, or combination of both EE and LAS. These results indicate there was no synergistic or antagonistic effect in bone mass when EE and LAS are given in combination at their fully efficacious doses.

SUMMARY AND CONCLUSIONS

LAS alone, EE alone, or combination of EE and LAS, completely prevented OVX-induced bone loss when administered at the fully efficacious doses.

Prevention of bone loss in lasofoxifene-treated OVX rats was achieved by the inhibition of bone resorption

- (decreased osteoclast number and surface) and bone turnover (decreased bone formation rate/bone surface) associated with OVX. The tissue level mechanism for the bone protective effects of EE and LAS appear to be similar.
- No synergistic or antagonistic effects were seen in bone mass and dynamic histomorphometric parameters when co-administration of EE and LAS.
- LAS antagonized the uterine hypertrophy effects induced by EE when co-administration was given to OVX rats.
- Our data support the strategy of using a SERM for antagonizing the estrogen's uterine effects but maintaining the bone protective effect of estrogen for the treatment of postmenopausal osteoporosis.

REFERENCES

1. Lobo A 1995 Benefits and risks of estrogen replacement therapy. Am J Obstet Gynecol 173:982–990.
2. Bryant H U, Glasebrook A L, Yang N N, Sato M 1996 A pharmacological review of raloxifene. J Bone Miner Metab 14:1–9.
3. Ke H Z, Chen H K, Simmons H A, Qi H, Crawford D T, Pirie C M, Chidsey-Frink K L, Ma Y F, Jee W S S, Thompson D D 1997 Comparative effects of droloxifene, tamoxifen, and estrogen on bone, serum cholesterol, and uterine hisotlogy in the ovariectomized rat model. Bone 20:31–39.
4. Cosman F, Lindsay R 1999 Selective estrogen receptor modulators: clinical spectrum. Endocrine Review 20:418–434.
5. Ke H Z, Paralkar V M, Grasser W A, Crawford D T, Qi H, Simmons H A, Pirie C M, Chidsey-Frink K L, Owen T A, Smock S L, Chen H K, Jee W S S, Cameron K O, Rosati R L, Brown T A, DaSilva-Jardine P, Thompson D D 1998 Effects of CP-336,156, a new, nonsteroidal estrogen agonist/antagonist, on bone, serum cholesterol, uterus, and body composition in rat models. Endocrinology 139:2068–2076.
6. Baron R, Vignery A, Neff L, Silverglate A, Maria A S 1983 Processing of undecalcified bone specimens for bone histomorphometry. In: Recker R R (ed) Bone Histomorphometry: Techniques and Interpretation. CRC Press, Boca Raton, Fla., pp 13–36.
7. Parfitt A M, Drezner M K, Glorieux F H, Kanis J A, Malluche H, Meunier P J, Ott S M, Recker R R 1987 Bone Histomorphometry: standardization of nomenclature, symbols and units. J Bone Miner Res 2:595–610.
8. Jee W S S, Inoue J, Jee K W, Haba T 1983 Histomorphometric assay of the growing long bone. In: Takahashi H (ed) Handbook of Bone Morphology. Nishimusa, Niigata City, Japan, pp 101–122.

What is claimed is:

1. A method of enhancing libido in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen, provided said patient does not have vaginal atrophy.

2. A method of enhancing libido in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin, provided said patient does not have vaginal atrophy.

3. A method of treating hypoactive sexual desire disorder in a patient, the method comprising administering to a patient in need thereof a therapeutically effective amonut of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen, provided said patient does not have vaginal atrophy.

4. A method of treating hypoactive sexual desire disorder in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin, provided said patient does not have vaginal atrophy.

5. A method of treating sexual arousal disorder in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen, provided said patient does not have vaginal atrophy.

6. A method of treating sexual arousal disorder in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin, provided said patient does not have vaginal atrophy.

7. A method of treating dyspareunia in a patient, the method comprising administering to a patient in need thereof a therapeutically effective amonut of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen, provided said patient does not have vaginal atrophy.

8. A method of treating dyspareunia in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin, provided said patient does not have vaginal atrophy.

9. A method of increasing the frequency and intensity of orgasms in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof and an estrogen, provided said patient does not have vaginal atrophy.

10. A method of increasing the frequency and intensity of orgasms in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin, provided said patient does not have vaginal atrophy.

11. A method of treating vaginismus in a patient, the method comprising administering to a patient in need thereof a therapeutically effective amount of (−)-cis-6-phenyl-5-[4-(2-pyrrolidin-1-yl-ethoxy)-phenyl]-5,6,7,8-tet rahydro-naphthalene-2-ol or a pharmacologically acceptable acid addition salt thereof and an estrogen, provided said patient does not have vaginal atrophy.

12. A method of treating vaginismus in a patient, the method comprising administering to a patient in need thereof a therapeutically effective amount of (−)-cis-6-phenyl-5-[4-(2-pyrrolidin-1-yl-ethoxy)-phenyl]-5,6,7,8-tetrahydro-naphthalene-2-ol or a pharmacologically acceptable acid addition salt thereof, an estrogen and a progestin, provided said patient does not have vaginal atrophy.

* * * * *